(12) United States Patent
Herfert et al.

(10) Patent No.: US 12,083,496 B2
(45) Date of Patent: Sep. 10, 2024

(54) PROCESS FOR PRODUCING SUPERABSORBENTS

(71) Applicant: BASF SE, Ludwigshafen (DE)

(72) Inventors: Norbert Herfert, Shanghai (CN);
Bootsara Parchana, Rayong (TH);
Sunantha Kaenthong, Rayong (TH);
Stephan Bauer, Ludwigshafen (DE);
Thomas Daniel, Ludwigshafen (DE);
Katrin Baumann, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 201 days.

(21) Appl. No.: 17/046,033

(22) PCT Filed: Apr. 9, 2019

(86) PCT No.: PCT/EP2019/058927
§ 371 (c)(1),
(2) Date: Oct. 8, 2020

(87) PCT Pub. No.: WO2019/201669
PCT Pub. Date: Oct. 24, 2019

(65) Prior Publication Data
US 2021/0121852 A1 Apr. 29, 2021

(30) Foreign Application Priority Data
Apr. 20, 2018 (WO) ............... PCT/CN2018/083937

(51) Int. Cl.
*B01J 20/26* (2006.01)
*B01J 20/28* (2006.01)
*B01J 20/30* (2006.01)
*C08F 220/06* (2006.01)

(52) U.S. Cl.
CPC ....... *B01J 20/267* (2013.01); *B01J 20/28016* (2013.01); *B01J 20/3021* (2013.01); *B01J 20/3085* (2013.01); *C08F 220/06* (2013.01); *C08F 2800/10* (2013.01); *C08F 2810/20* (2013.01)

(58) Field of Classification Search
None
See application file for complete search history.

(56) References Cited

U.S. PATENT DOCUMENTS

| | | | |
|---|---|---|---|
| 2006/0089611 A1* | 4/2006 | Herfert | A61L 15/60 604/367 |
| 2013/0256593 A1 | 10/2013 | Herfert et al. | |
| 2013/0260988 A1 | 10/2013 | Herfert et al. | |
| 2016/0332140 A1* | 11/2016 | Bauer | B01J 20/28016 |
| 2017/0281423 A1 | 10/2017 | Panayotova et al. | |

FOREIGN PATENT DOCUMENTS

| | | |
|---|---|---|
| EP | 2112172 A1 | 10/2009 |
| EP | 2163302 A1 | 3/2010 |
| WO | WO-2006/109882 A1 | 10/2006 |
| WO | WO-2009/060062 A1 | 5/2009 |
| WO | WO-2011/113777 A1 | 9/2011 |
| WO | WO-2013/045163 A1 | 4/2013 |
| WO | WO-2013/144027 A1 | 10/2013 |
| WO | WO-2018/029045 A1 | 2/2018 |

OTHER PUBLICATIONS

Graham, et al., "Chapter 3—Commercial Processes for the Manufacture of Superabsorbent Polymers", Modern Superabsorbent Polymer Technology, ed. Buchholz, et al., 1998, pp. 69-117.
International Application No. PCT/EP2019/058927, International Search Report and Written Opinion, mailed Aug. 7, 2019.

* cited by examiner

*Primary Examiner* — Tanisha Diggs
(74) *Attorney, Agent, or Firm* — Element IP, PLC

(57) ABSTRACT

The invention relates to a process for producing long-term color stable superabsorbent polymer particles, comprising polymerization of a monomer solution, wherein the monomer solution comprises at least 0.01% by weight of 1-hydroxyethane-1,1-diphosphonic acid or a salt thereof and at least 0.01% by weight of 2-hydroxy-2-sulfonatoacetic acid or a salt thereof.

5 Claims, No Drawings

PROCESS FOR PRODUCING SUPERABSORBENTS

CROSS-REFERENCE TO RELATED APPLICATIONS

This is the U.S. national phase of International Application No. PCT/EP2019/058927, filed Apr. 9, 2019, which claims the benefit of International Application No. PCT/CN2018/083937, filed Apr. 20, 2018.

DESCRIPTION

The invention relates to a process for producing long-term color stable superabsorbent polymer particles, comprising polymerization of a monomer solution, wherein the monomer solution comprises at least 0.01% by weight of 1-hydroxyethane-1,1-diphosphonic acid or a salt thereof and at least 0.01% by weight of 2-hydroxy-2-sulfonatoacetic acid or a salt thereof.

Superabsorbent polymer particles are used to produce diapers, tampons, sanitary napkins and other hygiene articles, but also as water-retaining agents in market gardening. The superabsorbent polymer particles are often also referred to as "absorbent resins", "superabsorbents", "superabsorbent polymers", "absorbent polymers", "absorbent gelling materials", "hydrophilic polymers" or "hydrogels".

The production of superabsorbent polymer particles is described in the monograph "Modern Superabsorbent Polymer Technology", F. L. Buchholz and A. T. Graham, Wiley-VCH, 1998, pages 71 to 103.

The properties of superabsorbent polymer particles can be adjusted, for example, via the amount of crosslinker used. With increasing amount of crosslinker, the centrifuge retention capacity (CRC) falls and the absorption under a pressure of 21.0 g/cm$^2$ (AUL0.3 psi) passes through a maximum.

To improve the application properties, for example permeability of the swollen gel bed (SFC) in the diaper and absorption under a pressure of 49.2 g/cm$^2$ (AUL0.7 psi), superabsorbent polymer particles are generally surface post-crosslinked. This increases the degree of crosslinking of the particle surface, which allows the absorption under a pressure of 49.2 g/cm$^2$ (AUL0.7 psi) and the centrifuge retention capacity (CRC) to be at least partly de-coupled. This surface post-crosslinking can be performed in the aqueous gel phase. Preferably, however, dried, ground and screened-off polymer particles (base polymer) are surface coated with a surface post-crosslinker, thermally surface pos-tcrosslinked and dried. Crosslinkers suitable for this purpose are compounds which can form covalent bonds with at least two carboxylate groups of the superabsorbing polymer particles.

A problem which often occurs in superabsorbent polymer particles is that of discoloration, which occurs in the course of storage at elevated temperature or elevated air humidity. Such conditions often occur in the course of storage in tropical or subtropical countries. Under such conditions, superabsorbent polymer particles tend to yellow; they may even take on a brown or even almost black color. This discoloration of the actually colorless superabsorbent polymer particles is unsightly and undesired, since it is visible especially in the desired thin hygiene products, and consumers reject unsightly hygiene products. The cause of the discoloration has not been entirely clarified, but reactive compounds such as residual monomers from the polymerization, the use of some initiators, impurities in the monomers or in the neutralizing agent, surface post-crosslinkers or stabilizers in the monomers used appear to play a role.

In order to prevent discoloration, there have been disclosed a lot of additives in the prior art.

WO 2006/109882 A1 discloses addition of compounds including a phosphorous atom or a sulfur based reducing agent.

EP 2 112 172 A1 discloses a process for superabsorbent polymers by polymerization in the presence of an organic phosphorous compound.

EP 2 163 302 A1 discloses addition of a chelating agent and a phosphorous compound.

WO 2009/060062 A1 discloses the addition of a reducing agent based on sulfonic acids or salts thereof.

WO 2011/113777 A1 discloses addition of an organic 2-hydroxy acid or salt thereof and addition of an inorganic phosphoric acid or salt thereof.

WO 2013/045163 A1 discloses a process for superabsorbent polymers by polymerization in the presence of a chelating agent.

WO 2013/144027 A1 discloses addition of a sulfonic derivate to the monomer solution or prior to drying and addition of a phosphonic acid derivate after drying or after surface post-crosslinking.

WO 2018/029045 A1 discloses a process for superabsorbent polymers by polymerization in the presence of a hydroxy phosphonic acid or salt thereof and addition of aluminum cations before, during or after thermal surface post-crosslinking.

It was an object of the present invention to provide a process for producing superabsorbent polymer particles having an improved long-term color stability.

The object was achieved by a process for producing long-term color stable superabsorbent polymer particles, comprising polymerization of a monomer solution, comprising
  a) partly neutralized acrylic acid,
  b) at least one crosslinker,
  c) at least one initiator,
  d) at least 0.01% by weight of 1-hydroxyethane-1,1-diphosphonic acid or a salt thereof based on acrylic acid prior to neutralization and
  e) at least 0.01% by weight of 2-hydroxy-2-sulfonatoacetic acid or a salt thereof based on acrylic acid prior to neutralization, drying the resulting polymer gel, optionally grinding and classifying the resulting dried polymer gel and optionally thermally post-crosslinking and cooling the resulting polymer particles.

The monomer solution comprises preferably from 0.05 to 5% by weight, more preferably from 0.2 to 2% by weight, most preferably from 0.5 to 1% by weight, of 1-hydroxyethane-1,1-diphosphonic acid or a salt thereof.

The monomer solution comprises preferably from 0.025 to 1% by weight, more preferably from 0.045 to 0.5% by weight, most preferably from 0.05 to 0.2% by weight, of 2-hydroxy-2-sulfonatoacetic acid or a salt thereof.

In a preferred embodiment of the present invention, the superabsorbent polymer particles are thermally post-crosslinked.

The present invention based on the finding that there is a strong synergistic effect between 1-hydroxyethane-1,1-diphosphonic acid and 2-hydroxy-2-sulfonatoacetic acid if both are used as additives in the monomer solution.

The usage 2-hydroxy-2-sulfonatoacetic acid alone results in a very good initial color and an insufficient long-term color stability. Moreover it also shows a negative impact on the polymerization and drying, especially if higher amounts of 2-hydroxy-2-sulfonatoacetic acid are used.

The present invention further provides superabsorbent polymer particles obtainable by the process according to the invention.

The superabsorbent polymer particles produced by the process according to the invention have a centrifuge retention capacity (CRC) of typically at least 25 g/g, preferably at least 30 g/g, more preferably at least 35 g/g, especially preferably at least 40 g/g, most preferably at least 45 g/g. The centrifuge retention capacity (CRC) of the superabsorbent polymer particles is typically less than 60 g/g.

The superabsorbent polymer particles produced by the process according to the invention have a level of extractables of typically 25% by weight or less.

The superabsorbent polymer particles produced by the process according to the invention have a Hunter 60 value (HC60) after 28 days of aging at 60° C. and 86% relative humidity of typically at least 47, preferably at least 49, more preferably at least 51, especially preferably at least 53, most preferably at least 55. The Hunter 60 value (HC60) after 28 days of aging at 60° C. and 86% relative humidity of the superabsorbent polymer particles is typically less than 70.

The superabsorbent polymer particles produced by the process according to the invention have a Hunter 60 value (HC60) after 14 days of aging at 70° C. and 80% relative humidity of typically at least 32, preferably at least 34, more preferably at least 36, especially preferably at least 38, most preferably at least 40. The Hunter 60 value (HC60) after 14 days of aging at 70° C. and 80% relative humidity of the superabsorbent polymer particles is less than 60.

The superabsorbent polymer particles produced by the process according to the invention have a yellowness index (YI) of YI D1925 (2/C) after 14 days of aging at 70° C. and 80% relative humidity of typically not more than 37, preferably not more than 35, more preferably not more than 33, especially preferably not more than 31, most preferably not more than 29. The yellowness index (YI) of YI D1925 (2/C) after 14 days of aging at 70° C. and 80% relative humidity of the superabsorbent polymer particles is typically more than 20.

The present invention further provides superabsorbent polymer particles based on crosslinked partly neutralized acrylic acid.

The superabsorbent polymer particles comprise at least 0.01% by weight of 1-hydroxyethane-1,1-diphosphonic acid or a salt thereof and at least 0.01% by weight of 2-hydroxy-2-sulfonatoacetic acid or a salt thereof, wherein the 1-hydroxyethane-1,1-diphosphonic acid or a salt thereof and the 2-hydroxy-2-sulfonatoacetic acid or a salt thereof are homogenously distributed within the polymer particles.

The superabsorbent polymer particles according to the invention comprise preferably from 0.05 to 5% by weight, more preferably from 0.2 to 2% by weight, most preferably from 0.5 to 1% by weight, of 1-hydroxyethane-1,1-diphosphonic acid or a salt thereof.

The superabsorbent polymer particles according to the invention comprise preferably from 0.025 to 1% by weight, more preferably from 0.04 to 0.7% by weight, most preferably from 0.05 to 0.5% by weight, of 2-hydroxy-2-sulfonatoacetic acid or a salt thereof.

In a preferred embodiment of the present invention, the superabsorbent polymer particles are thermally post-crosslinked.

The superabsorbent polymer particles according to the invention have a centrifuge retention capacity (CRC) of typically at least 25 g/g, preferably at least 30 g/g, more preferably at least 35 g/g, especially preferably at least 40 g/g, most preferably at least 45 g/g. The centrifuge retention capacity (CRC) of the superabsorbent polymer particles is typically less than 60 g/g.

The superabsorbent polymer particles according to the invention have a level of extractables of typically 25% by weight or less.

The superabsorbent polymer particles according to the invention have a Hunter 60 value (HC60) after 28 days of aging at 60° C. of typically at least 47, preferably at least 49, more preferably at least 51, especially preferably at least 53, most preferably at least 55. The Hunter 60 value (HC60) after 28 days of aging at 60° C. of the superabsorbent polymer particles is typically less than 70.

The superabsorbent polymer particles according to the invention have a Hunter 60 value (HC60) after 14 days of aging at 70° C. and 80% relative humidity of typically at least 32, preferably at least 34, more preferably at least 36, especially preferably at least 38, most preferably at least 40. The Hunter 60 value (HC60) after 14 days of aging at 70° C. and 80% relative humidity of the superabsorbent polymer particles is less than 60.

The superabsorbent polymer particles according to the invention have a yellowness index (YI) of YI D1925 (2/C) after 14 days of aging at 70° C. and 80% relative humidity of typically not more than 37, preferably not more than 35, more preferably not more than 33, especially preferably not more than 31, most preferably not more than 29. The yellowness index (YI) of YI D1925 (2/C) after 14 days of aging at 70° C. and 80% relative humidity of the superabsorbent polymer particles is typically more than 20.

The production of the superabsorbents is described in detail hereinafter:

The superabsorbents are produced by polymerizing a monomer solution, and are typically water-insoluble.

Acrylic acid typically comprises polymerization inhibitors, preferably hydroquinone monoethers, as storage stabilizers.

The monomer solution comprises preferably up to 250 ppm by weight, preferably at most 130 ppm by weight, more preferably at most 70 ppm by weight, and preferably at least 10 ppm by weight, more preferably at least 30 ppm by weight and especially around 50 ppm by weight, of hydroquinone monoether, based in each case on acrylic acid prior to neutralization. For example, the monomer solution can be prepared by using acrylic acid with an appropriate content of hydroquinone monoether.

Preferred hydroquinone monoethers are hydroquinone monomethyl ether (MEHQ) and/or alpha-tocopherol (vitamin E).

Suitable crosslinkers b) are compounds having at least two groups suitable for crosslinking. Such groups are, for example, ethylenically unsaturated groups which can be polymerized free-radically into the polymer chain, and functional groups which can form covalent bonds with the acid groups of acrylic acid. In addition, polyvalent metal salts which can form coordinate bonds with at least two acid groups of acrylic acid are also suitable as crosslinkers b). Crosslinkers b) are preferably compounds having at least two polymerizable groups which can be polymerized free-radically into the polymer network. Suitable crosslinkers b) are, for example, ethylene glycol dimethacrylate, diethylene glycol diacrylate, polyethylene glycol diacrylate, allyl methacrylate, trimethylolpropane triacrylate, triallylamine, tetraallylammonium chloride, tetraallyloxyethane, as described in EP 0 530 438 A1, di- and triacrylates, as described in EP 0 547 847 A1, EP 0 559 476 A1, EP 0 632 068 A1, WO 93/21237 A1, WO 2003/104299 A1, WO 2003/104300 A1, WO 2003/104301 A1 and DE 103 31 450 A1, mixed acrylates which, as well as acrylate groups, comprise further ethylenically unsaturated groups, as described in DE 103 31 456 A1 and DE 103 55 401 A1, or crosslinker mixtures, as described, for example, in DE 195 43 368 A1, DE 196 46 484 A1, WO 90/15830 A1 and WO 2002/032962 A2.

Preferred crosslinkers b) are pentaerythrityl triallyl ether, tetraallyloxyethane, methylenebismethacrylamide, 15-tuply ethoxylated trimethylolpropane triacrylate, polyethylene glycol diacrylate, trimethylolpropane triacrylate and triallylamine.

Very particularly preferred crosslinkers b) are the polyethoxylated and/or -propoxylated glycerols which have been esterified with acrylic acid or methacrylic acid to give di- or triacrylates, as described, for example, in WO 2003/104301 A1. Di- and/or triacrylates of 3- to 10-tuply ethoxylated glycerol are particularly advantageous. Very particular preference is given to di- or triacrylates of 1- to 5-tuply ethoxylated and/or propoxylated glycerol. Most preferred are the triacrylates of 3- to 5-tuply ethoxylated and/or propoxylated glycerol, especially the triacrylate of 3-tuply ethoxylated glycerol.

The amount of crosslinker b) is preferably 0.05 to 1.5% by weight, more preferably 0.1 to 1% by weight and most preferably 0.3 to 0.6% by weight, based in each case on acrylic acid prior to neutralization. With rising crosslinker content, the centrifuge retention capacity (CRC) falls and the absorption under a pressure of 21.0 g/cm$^2$ passes through a maximum.

The initiators c) used may be all compounds which generate free radicals under the polymerization conditions, for example thermal initiators, redox initiators, photoinitiators. Suitable redox initiators are sodium peroxodisulfate/ascorbic acid, hydrogen peroxide/ascorbic acid, sodium peroxodisulfate/sodium bisulfite and hydrogen peroxide/sodium bisulfite. Preference is given to using mixtures of thermal initiators and redox initiators, such as sodium peroxodisulfate/hydrogen peroxide/ascorbic acid. However, the reducing component used is preferably disodium 2-hydroxy-2-sulfonatoacetate or a mixture of disodium 2-hydroxy-2-sulfinatoacetate, disodium 2-hydroxy-2-sulfonatoacetate and sodium bisulfite. Such mixtures are obtainable as Bruggolite® FF6 and Bruggolite® FF7 (Brüggemann Chemicals; Heilbronn; Germany).

Typically, an aqueous monomer solution is used. The water content of the monomer solution is preferably from 40 to 75% by weight, more preferably from 45 to 70% by weight and most preferably from 50 to 65% by weight. It is also possible to use monomer suspensions, i.e. monomer solutions with excess sodium acrylate. With rising water content, the energy requirement in the subsequent drying rises, and, with falling water content, the heat of polymerization can only be removed inadequately.

For optimal action, the preferred polymerization inhibitors require dissolved oxygen. The monomer solution can therefore be freed of dissolved oxygen before the polymerization by inertization, i.e. flowing an inert gas through, preferably nitrogen or carbon dioxide. The oxygen content of the monomer solution is preferably lowered before the polymerization to less than 1 ppm by weight, more preferably to less than 0.5 ppm by weight, most preferably to less than 0.1 ppm by weight.

For better control of the polymerization reaction, it is optionally possible to add all known chelating agents to the monomer solution or suspension or to the raw materials thereof. Suitable chelating agents are, for example, phosphoric acid, diphosphoric acid, triphosphoric acid, polyphosphoric acid, citric acid, tartaric acid, or salts thereof.

Further suitable examples are iminodiacetic acid, hydroxyethyliminodiacetic acid, nitrilotriacetic acid, nitrilotripropionic acid, ethylenediaminetetraacetic acid, diethylenetriaminepentaacetic acid, triethylenetetraaminehexaacetic acid, N,N-bis(2-hydroxyethyl)glycine and trans-1,2-diaminocyclohexanetetraacetic acid, and salts thereof. The amount used is typically 1 to 30 000 ppm based on the monomers a), preferably 10 to 1000 ppm, preferentially 20 to 600 ppm, more preferably 50 to 400 ppm, most preferably 100 to 300 ppm.

The monomer solution is polymerized. Suitable reactors are, for example, kneading reactors or belt reactors. In the kneader, the polymer gel formed in the polymerization of an aqueous monomer solution or suspension is comminuted continuously by, for example, contrarotatory stirrer shafts, as described in WO 2001/038402 A1. Polymerization on the belt is described, for example, in DE 38 25 366 A1 and U.S. Pat. No. 6,241,928. Polymerization in a belt reactor forms a polymer gel which has to be comminuted in a further process step, for example in an extruder or kneader.

To improve the drying properties, the comminuted polymer gel obtained by means of a kneader can additionally be extruded.

The acid groups of the resulting polymer gels have typically been partially neutralized. Neutralization is preferably carried out at the monomer stage. This is typically accomplished by mixing in the neutralizing agent as an aqueous solution or preferably also as a solid. The degree of neutralization is preferably from 50 to 85 mol %, more preferably from 60 to 80 mol % and most preferably from 65 to 75 mol %, for which the customary neutralizing agents can be used, preferably alkali metal hydroxides, alkali metal oxides, alkali metal carbonates or alkali metal hydrogencarbonates and also mixtures thereof. Instead of alkali metal salts, it is also possible to use ammonium salts. Particularly preferred alkali metals are sodium and potassium, but very particular preference is given to sodium hydroxide, potassium hydroxide and also mixtures thereof.

The resulting polymer gel is dried. The driers are not subject to any restriction. However, the drying of the polymer gel is preferably performed with a belt drier until the residual moisture content is preferably 0.5 to 10% by weight, more preferably 1 to 7% by weight and most preferably 2 to 5% by weight, the residual moisture content being determined by EDANA recommended test method No. WSP 230.2 (05) "Mass Loss Upon Heating". In the case of too high a residual moisture content, the dried polymer gel has too low a glass transition temperature $T_g$ and can be processed further only with difficulty. In the case of too low a residual moisture content, the dried polymer gel is too brittle and, in the subsequent grinding steps, undesirably large amounts of polymer particles with an excessively low particle size are obtained ("fines"). The solids content of the gel before the drying is preferably from 25 to 90% by weight, more preferably from 35 to 70% by weight and most preferably from 40 to 60% by weight. However, a fluidized bed drier or a paddle drier may optionally also be used for drying purposes.

Subsequently, the dried polymer gel is ground and classified. The apparatus used for grinding may typically be single- or multistage roll mills, preferably two- or three-stage roll mills, pin mills, hammer mills or vibratory mills.

The mean particle size of the polymer particles removed as the product fraction is preferably at least 200 µm, more preferably from 250 to 600 µm and very particularly from 300 to 500 µm. The mean particle size of the product fraction may be determined by means of EDANA recommended test method No. WSP 220.2 (05) "Particle Size Distribution", where the proportions by mass of the screen fractions are plotted in cumulated form and the mean particle size is determined graphically. The mean particle size here is the value of the mesh size which gives rise to a cumulative 50% by weight.

The proportion of particles with a particle size of at least 150 µm is preferably at least 90% by weight, more preferably at least 95% by weight, most preferably at least 98% by weight.

Polymer particles with too small a particle size lower the saline flow conductivity (SFC). The proportion of excessively small polymer particles ("fines") should therefore be low.

Excessively small polymer particles are therefore typically removed and recycled into the process. This is preferably done before, during or immediately after the polymerization, i.e. before the drying of the polymer gel. The excessively small polymer particles can be moistened with water and/or aqueous surfactant before or during the recycling.

It is also possible to remove excessively small polymer particles in later process steps, for example after the surface post-crosslinking or another coating step. In this case, the excessively small polymer particles recycled are surface post-crosslinked or coated in another way, for example with fumed silica or precipitated silica.

When a kneading reactor is used for polymerization, the excessively small polymer particles are preferably added during the last third of the polymerization.

When the excessively small polymer particles are added at a very early stage, for example actually to the monomer solution, this lowers the centrifuge retention capacity (CRC) of the resulting superabsorbents. However, this can be compensated for, for example, by adjusting the amount of crosslinker b) used.

When the excessively small polymer particles are added at a very late stage, for example not until an apparatus connected downstream of the polymerization reactor, for example an extruder, the excessively small polymer particles can be incorporated into the resulting polymer gel only with difficulty. Insufficiently incorporated, excessively small polymer particles are, however, detached again from the dried polymer gel during the grinding, are therefore removed again in the course of classification and increase the amount of excessively small polymer particles to be recycled.

The proportion of particles having a particle size of at most 850 µm is preferably at least 90% by weight, more preferably at least 95% by weight, most preferably at least 98% by weight.

The proportion of particles having a particle size of at most 600 µm is preferably at least 90% by weight, more preferably at least 95% by weight, most preferably at least 98% by weight.

Polymer particles of excessively large particle size lower the free swell rate (FSR). The proportion of excessively large polymer particles should therefore likewise be small.

Excessively large polymer particles are therefore typically removed and recycled into the grinding of the dried polymer gel.

To improve the properties, the polymer particles may subsequently be thermally surface post-crosslinked. Suitable surface post-crosslinkers are compounds which comprise groups which can form covalent bonds with at least two acid groups of the polymer particles. Suitable compounds are, for example, polyfunctional amines, polyfunctional amido amines, polyfunctional epoxides, as described in EP 0 083 022 A2, EP 0 543 303 A1 and EP 0 937 736 A2, di- or polyfunctional alcohols, as described in DE 33 14 019 A1, DE 35 23 617 A1 and EP 0 450 922 A2, or β-hydroxyalkylamides, as described in DE 102 04 938 A1 and U.S. Pat. No. 6,239,230.

Additionally described as suitable surface post-crosslinkers are cyclic carbonates in DE 40 20 780 C1,2-oxazolidinone and derivatives thereof, such as 2-hydroxyethyl-2-oxazolidinone, in DE 198 07 502 A1, bis- and poly-2-oxazolidinones in DE 198 07 992 C1,2-oxotetrahydro-1,3-oxazine and derivatives thereof in DE 198 54 573 A1, N-acyl-2-oxazolidinones in DE 198 54 574 A1, cyclic ureas in DE 102 04 937 A1, bicyclic amide acetals in DE 103 34 584 A1, oxetanes and cyclic ureas in EP 1 199 327 A2 and morpholine-2,3-dione and derivatives thereof in WO 2003/031482 A1.

Preferred surface post-crosslinkers are ethylene carbonate, ethylene glycol diglycidyl ether, reaction products of polyamides with epichlorohydrin and mixtures of propylene glycol and 1,4-butanediol.

Very particularly preferred surface post-crosslinkers are 2-hydroxyethyloxazolidin-2-one, oxazolidin-2-one and 1,3-propanediol.

In addition, it is also possible to use surface post-crosslinkers which comprise additional polymerizable ethylenically unsaturated groups, as described in DE 37 13 601 A1.

The amount of surface post-crosslinker is preferably 0.001 to 2% by weight, more preferably 0.02 to 1% by weight and most preferably 0.05 to 0.2% by weight, based in each case on the polymer particles.

In a preferred embodiment of the present invention, polyvalent cations are applied to the particle surface in addition to the surface post-crosslinkers before, during or after the surface post-crosslinking.

The polyvalent cations usable in the process according to the invention are, for example, divalent cations such as the cations of zinc, magnesium, calcium, iron and strontium, trivalent cations such as the cations of aluminum, iron, chromium, rare earths and manganese, tetravalent cations such as the cations of titanium and zirconium. Possible counterions are chloride, bromide, sulfate, hydrogensulfate, carbonate, hydrogencarbonate, nitrate, phosphate, hydrogenphosphate, dihydrogenphosphate and carboxylate, such as acetate and lactate. Aluminum sulfate and aluminum lactate are preferred. Apart from metal salts, it is also possible to use polyamines as polyvalent cations.

The amount of polyvalent cation used is, for example, 0.001 to 1.5% by weight, preferably 0.005 to 1% by weight and more preferably 0.02 to 0.8% by weight, based in each case on the polymer particles.

The surface post-crosslinking is typically performed in such a way that a solution of the surface post-crosslinker is sprayed onto the dried polymer particles. After the spray application, the polymer particles coated with surface post-crosslinker are dried thermally, and the surface post-crosslinking reaction can take place either before or during the drying.

The spray application of a solution of the surface post-crosslinker is preferably performed in mixers with moving mixing tools, such as screw mixers, disk mixers and paddle mixers. Particular preference is given to horizontal mixers such as paddle mixers, very particular preference to vertical mixers. The distinction between horizontal mixers and vertical mixers is made by the position of the mixing shaft, i.e. horizontal mixers have a horizontally mounted mixing shaft and vertical mixers a vertically mounted mixing shaft. Suitable mixers are, for example, horizontal Pflugschar® plowshare mixers (Gebr. Lödige Maschinenbau GmbH; Paderborn; Germany), Vrieco-Nauta continuous mixers (Hosokawa Micron BV; Doetinchem; the Netherlands), Processall Mixmill mixers (Processall Incorporated; Cincinnati; USA) and Schugi Flexomix® (Hosokawa Micron BV; Doetinchem; the Netherlands). However, it is also possible to spray on the surface post-crosslinker solution in a fluidized bed.

The surface post-crosslinkers are typically used in the form of an aqueous solution. The penetration depth of the surface post-crosslinker into the polymer particles can be adjusted via the content of non-aqueous solvent and total amount of solvent.

When exclusively water is used as the solvent, a surfactant is advantageously added. This improves the wetting behavior and reduces the tendency to form lumps. However, preference is given to using solvent mixtures, for example isopropanol/water, 1,3-propanediol/water and propylene glycol/water, where the mixing ratio in terms of mass is preferably from 20:80 to 40:60.

The thermal surface post-crosslinking is preferably performed in contact driers, more preferably paddle driers, most preferably disk driers. Suitable driers are, for example, Hosokawa Bepex® Horizontal Paddle Dryer (Hosokawa Micron GmbH; Leingarten; Germany), Hosokawa Bepex® Disc Dryer (Hosokawa Micron GmbH; Leingarten; Germany) and Nara Paddle Dryer (NARA Machinery Europe; Frechen; Germany). Moreover, fluidized bed driers may also be used.

The thermal surface post-crosslinking can be effected in the mixer itself, by heating the jacket or blowing in warm air. Equally suitable is a downstream drier, for example a shelf drier, a rotary tube oven or a heatable screw. It is particularly advantageous to effect mixing and drying in a fluidized bed drier.

Preferred surface post-crosslinking temperatures are in the range of 100 to 250° C., preferably 110 to 230° C., more preferably 120 to 210° C. and most preferably 130 to 190° C. The preferred residence time at this temperature in the reaction mixer or drier is preferably at least 20 minutes, more preferably at least 40 minutes, most preferably at least 60 minutes, and typically at most 150 minutes.

Subsequently, the surface post-crosslinked polymer particles can be classified again, excessively small and/or excessively large polymer particles being removed and recycled into the process.

To further improve the properties, the surface post-crosslinked polymer particles can be coated or remoisturized.

The remoisturizing is preferably performed at 30 to 80° C., more preferably at 35 to 70° C., most preferably at 40 to 60° C. At excessively low temperatures, the superabsorbents tend to form lumps, and, at higher temperatures, water already evaporates to a noticeable degree. The amount of water used for remoisturizing is preferably from 1 to 10% by weight, more preferably from 2 to 8% by weight and most preferably from 3 to 5% by weight. The remoisturizing increases the mechanical stability of the polymer particles and reduces their tendency to static charging.

Suitable coatings for improving the free swell rate and the saline flow conductivity (SFC) are, for example, inorganic inert substances, such as water-insoluble metal salts, organic polymers, cationic polymers and di- or polyvalent metal cations. Suitable coatings for dust binding are, for example, polyols. Suitable coatings for counteracting the undesired caking tendency of the polymer particles are, for example, fumed silica, such as Aerosil® 200, or precipitated silica, such as Sipernat® D17, and surfactants, such as Span® 20.

Methods:

The measurements should, unless stated otherwise, be carried out at an ambient temperature of 23±2° C. and a relative atmospheric humidity of 50±10%. The superabsorbent polymers are mixed thoroughly before the measurement.

Vortex 50.0±1.0 ml of 0.9% NaCl solution are added into a 100 ml beaker. A cylindrical stirrer bar (30×6 mm) is added and the saline solution is stirred on a stir plate at 60 rpm. 2.000±0.010 g of superabsorbent polymer particles are added to the beaker as quickly as possible, starting a stop watch as addition begins. The stopwatch is stopped when the surface of the mixture becomes "still" that means the surface has no turbulence, and while the mixture may still turn, the entire surface of particles turns as a unit. The displayed time of the stopwatch is recorded as Vortex time.

Residual Monomers

The residual monomers in superabsorbent polymer particles are determined by EDANA recommended test method No. WSP 210.2 (04) "Determination of the Amount of Residual Monomers in Superabsorbent Materials".

Particle Size Distribution

The particle size distribution of the superabsorbent polymer particles is determined by the EDANA recommended test method No. WSP 220.2 (05) "Determination of Polyacrylate Superabsorbent Powders and Particle Size Distribution-Sieve Fractionation".

D50 is the diameter of the particle that 50% of a sample's mass is smaller than and 50% of a sample's mass is larger than.

Moisture Content (MC)

The moisture content of the superabsorbent polymer particles is determined by the EDANA recommended test method No. WSP 230.2 (05) "Moisture Content-Weight Loss Upon Heating".

Free Swell Capacity (FSC)

The free swell capacity of superabsorbent polymer particles is determined analogously to the EDANA recommended test method No. WSP 240.2 (05) "Free Swell Capacity in Saline by Gravimetric Determination". For measuring the free swell capacity (FSC 1 min) the superabsorbent polymer particles are placed in tea bags. The tea bags are taken in 1 s under the surface of the 0.9% NaCl solution (minimum 100 ml for each tea bag) for 1 minute, followed by a hanging time of 5 minutes. The free swell capacity is defined as $$FSC[g/g] = \frac{(m_{wi} - m_b) - m_{si}}{m_{si}}$$

where $m_{si}$ is the mass of the superabsorbent polymer particles, $m_b$ is the average mass, of the wet blank bag and $m_{wi}$ is the mass of the wet bag containing superabsorbent polymer.

Centrifuge Retention Capacity (CRC)

The centrifuge retention capacity of superabsorbent polymer particles is determined by the EDANA recommended test method No. WSP 241.2 (05) "Gravimetric Determination of Fluid Retention Capacity in Saline Solution After Centrifugation", wherein for higher values of the centrifuge retention capacity lager tea bags have to be used.

Absorbency Under No Load (AUNL)

The absorbency under no load of the superabsorbent polymer particles is determined analogously to the EDANA recommended test method No. WSP 242.2 (05) "Gravimetric Determination of Absorption Under Pressure", except using a weight of 0.0 g/cm$^2$ instead of a weight of 21.0 g/cm$^2$.

Absorbency Under Load (AUL)

The absorbency under load of the superabsorbent polymer particles is determined by the EDANA recommended test method No. WSP 242.2 (05) "Gravimetric Determination of Absorption Under Pressure".

Absorbency Under High Load (AUHL)

The absorbency under high load of the superabsorbent polymer particles is determined analogously to the EDANA recommended test method No. WSP 242.2 (05) "Gravimetric Determination of Absorption Under Pressure", except using a weight of 49.2 g/cm$^2$ instead of a weight of 21.0 g/cm$^2$.

Flow Rate

The flow rate of the superabsorbent polymer particles is determined by the EDANA recommended test method No. WSP 250.2 (05) "Gravimetric Determination of Flowrate".

Bulk Density

The bulk density of the superabsorbent polymer particles is determined by the EDANA recommended test method No. WSP 260.2 (05) "Gravimetric Determination of Density".

Extractables (Ext. 1 h)

The content of extractable constituents in superabsorbent polymer particles is determined analogously to the EDANA recommended test method No. WSP 270.2 (05) "Determination of Extractable Polymer Content by Potentiometric Titration", except stirring for 1 hour instead of stirring for 16 hours.

Extractables (Ext. 16 h)

The content of extractable constituents in superabsorbent polymer particles is determined by the EDANA recommended test method No. WSP 270.2 (05) "Determination of Extractable Polymer Content by Potentiometric Titration".

SAP Rewet 1.000 g of superabsorbent polymer particles are sprinkled homogeneous into a petri dish with a diameter of 7 cm. 25 ml of 0.9% NaCl solution is added onto the superabsorbent polymer particles in the petri dish. After 30 seconds, the petri dish is gently moved back and forth to get a flat surface of swollen gel. After the testing time of 3 minutes, 10 or more filter papers (diameter of 5.5 cm marked with the weight) are put onto the swollen gel bed and a weight of 0.3 psi (as used for AUL measurement) is put onto the filter papers. After 1 minute, the weight is removed and the filter papers from the swollen gel bed. All gel particles sticking to the filter papers are removed from the filter paper. The SAP Rewet is the differences of the wet weigh filter papers to the dry weight of the filter papers.

Roundness

The roundness is determined with the PartAn® 3001 L Particle Analysator (Microtrac Europe GmbH; Meerbusch; Germany). The roundness is defined as $$\text{Roundness} = \frac{4\pi A}{U^2}$$

where A is the cross-sectional area and U is the cross-sectional circumference of the polymer particles. The roundness is the volume-average roundness.

For the measurement, the superabsorbent polymer particles are introduced through a funnel and conveyed to the falling shaft with a metering channel. While the particles fall past a light wall, they are recorded selectively by a camera. The images recorded are evaluated by the software in accordance with the parameters selected.

Caking (40° C./80% r.h./1 h)

5 g of the superabsorbent polymer particles are placed in an aluminum weighing dish (57 mm×15 mm) and stored for 1 hour at 40° C. and 80% relative humidity. The samples are cooled down to ambient temperature and weighed. After sieving over a sieve of 1.68 mm hole size (ASTM No. 12, Diameter of the sieve >57 mm and <100 mm), the amount which passes through the sieve is weighed to determine the mass of the non-caking polymer particles. The sieving process is described as follows:

Carefully take the aluminum dish containing hydrated polymer and hold upright in one hand. Invert the sieve-pan assembly over the dish and in one continuous motion, gently invert the sieve, pan and weighing dish-containing polymer, such that the dish is now inverted on top of the sieve screen. Add the lid to the sieve screen including the aluminum weighing dish and place the assembly in the sieve shaker. Vibrate the sieve assembly for one minute at 0.20 mm amplitude with a Retsch® Vibratory Sieve Shaker AS 200 control.

The percent of the particles which are non-caking is then determined by the following formula:

$$\text{Caked Polymer (\%)} = 100 - \left(\left(\frac{W_{UNC} - W_{PAN}}{W_{HYD} - W_d}\right) \times 100\right)$$

where $W_d$ is the weight of aluminum dish, $W_{HYD}$ is the weight of hydrated polymer plus aluminum dish before sifting, WPAN is the weight of the collection pan and $W_{UNC}$ is the weight of collection pan and hydrated polymer.

Color Value (CIE Color Numbers [L, a, b])

Measurement of the color value is done by means of a colorimeter model "LabScan XE Spectrometer" (Hunter-Lab; Reston; U.S.A.) according to the CIELAB procedure (Hunterlab, Volume 8, 1996, Issue 7, pages 1 to 4). Colors are described by the coordinates L, a, and b of a three-dimensional system. L characterizes the brightness, whereby L=0 is black and L=100 is white. The values for a and b describe the position of the color on the color axis red/green resp. yellow/blue, whereby positive a values stand for red colors, negative a values for green colors, positive b values for yellow colors, and negative b values for blue colors.

The Hunter 60 value (HC60) is a measure of the whiteness of surfaces and is defined as L-3b, i.e., the lower the value, the darker and the yellower the color is.

The Yellowness Index (YI) of YI D1925 (2/C) is measured per ASTM D-1925, 2 deg./III. ° C. As higher the value as darker and yellower the color is.

The test was done using a Tissue Culture Dish (diameter of 35 mm and height of 10 mm) and a Port Plate Opening of 0.5 inch.

The measurement of the color value is in agreement with the tristimulus method according to DIN 5033-6.

EXAMPLES

Example 1 (Inventive)

A 2 L stainless steel vessel was initially charged with 284.46 g of 50% by weight sodium hydroxide solution and 552.12 g of deionized water. The mixture was cooled down to 15° C. by means of a cooling bath. Then 251.21 g of initially part of acrylic acid were added while stirring. The rate of addition was adjusted in such way that the temperature did not exceed 35° C. After addition, the mixture was kept at approximately 35° C. for 2 minutes. Thereafter, additional 90.43 g of second part of acrylic acid were added under stirring keeping the temperature of the mixture below 35° C. The degree of neutralization was 75 mol-%. After addition of the second portion of acrylic acid, the mixture was cooled down to 20° C. and 0.72 g of 15-fold ethoxylated trimethylolpropane triacrylate were added under stirring. Then 0.036 g of 2-hydroxy-2-methylpropiophenone and 0.012 g of 2,2-dimethoxy-1,2-diphenylethan-1-one were added under stirring and the mixture was cooled down to 15° C. The mixture was freed of oxygen by passing nitrogen through via a glass frit while cooling down the mixture to 7° C. Then 5.12 g of aqueous disodium 2-hydroxy-2-sulfonato acetic acid (as 5% by weight aqueous solution), 10.25 g of aqueous disodium 1-hydroxyethane-1,1-diphosphonic acid (as 20% by weight aqueous solution) and 5.64 of aqueous sodium peroxodisulfate (as 10% by weight aqueous solution) were added subsequently to the monomer solution. The monomer solution was transferred to a glass dish. The dimensions of the glass dish were such that a layer thickness of the monomer solution of 5 cm was established. The mixture polymerized by placing the glass dish with the monomer solution under a UV lamp (UV intensity=25 mW/cm$^2$) for 11.5 minutes and turning off the UV lamp for another 4.5 minutes (total reaction time 16 minutes). The resulting gel was ground with the aid of a commercial meat grinder with a 6 mm perforated disk. 3.42 g of aqueous sodium bisulfite (as 5% by weight aqueous solution) was sprayed onto the ground gel and the gel was passed through the meat grinder two more times. The resulting gel was dried in a laboratory drying cabinet at 180° C. for 60 minutes. The product was then ground by means of an ultra-centrifugal mill (Retsch model ZM100 with 12-tooth rotor and 1.5 mm ring sieve; speed at 14000 rpm) and the sieve fraction of 150 to 710 μm was obtained by sieving of the milled product.

The superabsorbent particles were analyzed. The data are shown in table 1.

4 g of the superabsorbent particles were stored for 28 days at 60° C. and a relative humidity of 86%. The initial color and the color after storage were determined. The data are shown in table 2.

Examples 2 and 3 (not Inventive)

Example 1 was repeated, except the disodium 2-hydroxy-2-sulfonato acetic acid or disodium 1-hydroxyethane-1,1-diphosphonic acid was not added. The data are shown in tables 1 and 2.

TABLE 1

Analytical data

| Example Unit | HDPA wt. % boaa | HSAA wt. % boaa | MC wt. % | CRC g/g | RAA wt. % | Ext. 1 h wt. % | Ext. 16 h wt. % | Vortex s |
|---|---|---|---|---|---|---|---|---|
| 1 | 0.60 | 0.075 | 2.7 | 45.7 | 0.025 | 18.4 | 22.2 | 30 |
| 2 | 0.60 |  | 2.6 | 45.7 | 0.033 | 15.5 | 20.8 | 37 |
| 3 |  | 0.075 | 3.4 | 41.3 | 0.045 | 13.7 | 18.1 | 35 |

TABLE 2

Color stability

| Example Unit | HDPA wt. % boaa | HSAA wt. % boaa | L initial | L 28 d | a initial | a 28 d | b initial | b 28 d | HC60 initial | HC60 28 d |
|---|---|---|---|---|---|---|---|---|---|---|
| 1 | 0.60 | 0.075 | 83.8 | 78.1 | −1.0 | −0.5 | 9.0 | 7.7 | 56.8 | 55.0 |
| 2 | 0.60 |  | 83.1 | 74.6 | −0.5 | 0.2 | 9.7 | 9.6 | 54.0 | 45.8 |
| 3 |  | 0.075 | 86.3 | 71.6 | −0.7 | 0.5 | 7.5 | 10.7 | 63.8 | 39.5 |

HDPA: disodium 1-hydroxyethane-1,1-diphosphonic acid
HSAA: disodium 2-hydroxy-2-sulfonato acetic acid
boaa: based on acrylic acid Examples 4 to 10

Example 1 was repeated, except that different amounts of disodium 2-hydroxy-2-sulfonato acetic acid and disodium 1-hydroxyethane-1,1-diphosphonic acid were added. The data are shown in table 3.

4 g of the superabsorbent particles were stored for 28 days at 60° C. and a relative humidity of 86%. The initial color and the color after storage were determined. The data are shown in table 4.

TABLE 3

Analytical data

| Example Unit | HDPA wt. % boaa | HSAA wt. % boaa | MC wt. % | CRC g/g | RAA wt. % | Ext. 1 h wt. % | Ext. 16 h wt. % | Vortex s |
|---|---|---|---|---|---|---|---|---|
| 4*) | 0.60 |  | 2.6 | 45.7 | 0.033 | 15.5 | 20.8 | 37 |
| 5 | 0.50 | 0.10 | 3.2 | 47.9 | 0.024 | 17.8 | 24.0 | 37 |
| 6 | 0.40 | 0.20 | 3.4 | 48.8 | 0.023 | 20.8 | 26.1 | 38 |
| 7 | 0.30 | 0.30 | 3.5 | 47.8 | 0.021 | 20.9 | 26.8 | 32 |
| 8 | 0.20 | 0.40 | 3.9 | 48.6 | 0.024 | 21.4 | 27.4 | 36 |
| 9 | 0.10 | 0.50 | 3.4 | 48.3 | 0.025 | 20.2 | 27.9 | 31 |
| 10*)**) |  | 0.60 | 3.7 | 48.5 | 0.115 | 26.6 | 30.8 | 32 |

TABLE 4

Color stability

| Example Unit | HDPA wt. % boaa | HSAA wt. % boaa | L initial | L 28 d | a initial | a 28 d | b initial | b 28 d | HC60 initial | HC60 28 d |
|---|---|---|---|---|---|---|---|---|---|---|
| 4*) | 0.60 |  | 83.1 | 74.6 | −0.5 | 0.2 | 9.7 | 9.6 | 54.0 | 45.8 |
| 5 | 0.50 | 0.10 | 85.0 | 78.1 | −1.0 | −0.6 | 9.0 | 7.6 | 58.0 | 55.3 |
| 6 | 0.40 | 0.20 | 86.8 | 79.9 | −1.0 | −0.9 | 7.8 | 6.7 | 63.4 | 59.8 |
| 7 | 0.30 | 0.30 | 82.6 | 77.4 | −1.2 | −0.9 | 7.9 | 6.5 | 58.9 | 57.9 |
| 8 | 0.20 | 0.40 | 85.2 | 77.8 | −1.3 | −0.7 | 7.9 | 6.3 | 61.5 | 58.9 |
| 9 | 0.10 | 0.50 | 87.0 | 78.1 | −1.3 | −0.7 | 7.7 | 6.6 | 63.9 | 58.3 |
| 10*)**) |  | 0.60 | 85.1 | 68.5 | −1.5 | −0.5 | 6.7 | 8.7 | 65.0 | 42.4 |

HDPA: disodium 1-hydroxyethane-1,1-diphosphonic acid
HSAA: disodium 2-hydroxy-2-sulfonato acetic acid
boaa: based on acrylic acid
) comparative example
*) polymer gel very sticky and difficult drying Example 11 (not Inventive)

The example was done analogously to Example 1 of WO 2016/134905 A1.

The process was performed in a concurrent spray drying plant with an integrated fluidized bed (27) as shown in FIG. 1 of WO 2016/134905 A1. The reaction zone (5) had a height of 22 m and a diameter of 3.4 m. The internal fluidized bed (IFB) had a diameter of 3 m and a weir height of 0.25 m.

The drying gas was fed via a gas distributor (3) at the top of the spray dryer. The drying gas was partly recycled (drying gas loop) via a cyclone as dust separation unit (9) and a condenser column (12). The drying gas was nitrogen that comprises from 1% to 4% by volume of residual oxygen. Prior to the start of polymerization the drying gas loop was filled with nitrogen until the residual oxygen was below 4% by volume. The gas velocity of the drying gas in the reaction zone (5) was 0.79 m/s. The pressure inside the spray dryer was 4 mbar below ambient pressure.

The temperature of the gas leaving the reaction zone (5) was measured at three points around the circumference at the end of the cylindrical part of the spray dryer as shown in FIG. 3 of WO 2016/134905 A1. Three single measurements (43) were used to calculate the average temperature (spray dryer outlet temperature). The drying gas loop was heated up and the dosage of monomer solution is started up. From this time the spray dryer outlet temperature was controlled to 118° C. by adjusting the gas inlet temperature via the heat exchanger (20). The gas inlet temperature was 179° C. and the steam content of the drying gas is shown in table 5.

The product accumulated in the internal fluidized bed (27) until the weir height was reached. Conditioned internal fluidized bed gas having a temperature of 106° was fed to the internal fluidized bed (27) via line (25). The gas velocity of the internal fluidized bed gas in the internal fluidized bed (27) was 0.65 m/s. The residence time of the product was 150 min. The temperature of the superabsorbent polymer particles in the internal fluidized bed (27) was 78° C.

The spray dryer offgas was filtered in cyclone as dust separation unit (9) and sent to a condenser column (12) for quenching/cooling. Excess water was pumped out of the condenser column (12) by controlling the (constant) filling level inside the condenser column (12). The water inside the condenser column (12) was cooled by a heat exchanger (13) and pumped counter-current to the gas. The temperature and the steam content of the gas leaving the condenser column (12) are shown in table 5. The water inside the condenser column (12) was set to an alkaline pH by dosing sodium hydroxide solution to wash out acrylic acid vapors.

The gas leaving the condenser column (12) was split to the drying gas inlet pipe (1) and the conditioned internal fluidized bed gas (25). The gas temperatures were controlled via heat exchangers (20) and (22). The hot drying gas was fed to the concurrent spray dryer via gas distributor (3). The gas distributor (3) consists of a set of plates providing a pressure drop of 2 to 4 mbar depending on the drying gas amount.

The product was discharged from the internal fluidized bed (27) via rotary valve (28) into sieve (29). The sieve (29) was used for sieving off overs/lumps having a particle diameter of more than 800 μm.

The monomer solution was prepared by mixing first acrylic acid with 3-tuply ethoxylated glycerol triacrylate (internal crosslinker), secondly with 37.3% by weight sodium acrylate solution and thirdly with aqueous of disodium 1-hydroxyethane-1,1-diphosphonic acid (HDPA). The temperature of the resulting monomer solution was controlled to 10° C. by using a heat exchanger and pumping in a loop. A filter unit having a mesh size of 250 μm was used in the loop after the pump. The initiators were metered into the monomer solution upstream of the dropletizer by means of static mixers (31) and (32) via lines (33) and (34) as shown in FIG. 1 of WO 2016/134905 A1. sodium peroxodisulfate solution having a temperature of 20° C. was added via line (33) and [2,2'-azobis[2-(2-imidazolin-2-yl)propane] dihydrochloride solution together was added via line (34). Each initiator was pumped in a loop and dosed via control valves to each dropletizer unit. A second filter unit having a mesh size of 140 μm was used after the static mixer (32). For dosing the monomer solution into the top of the spray dryer three dropletizer units were used as shown in FIG. 4 of WO 2016/134905 A1.

A dropletizer unit consisted of an outer pipe (47) having an opening for the dropletizer cassette (49) as shown in FIG. 5 of WO 2016/134905 A1. The dropletizer cassette (49) was connected with an inner pipe (48). The inner pipe (48) having a PTFE block (50) at the end as sealing can be pushed in and out of the outer pipe (47) during operation of the process for maintenance purposes.

The dropletizer cassette (49) had 508 bores having a diameter of 120 μm and a bore spacing of 8 mm. The dropletizer cassette (49) consisted of a flow channel (56) having essential no stagnant volume for homogeneous distribution of the premixed monomer and initiator solutions and one droplet plate (53). The droplet plate (53) had an angled configuration with an angle of 3°. The droplet plate (53) was made of stainless steel and had a length of 630 mm, a width of 128 mm and a thickness of 1 mm.

The feed to the spray dryer consisted of 10.45% by weight of acrylic acid, 33.40% by weight of sodium acrylate, 0.018% by weight of 3-tuply ethoxylated glycerol triacrylate, 0.108% by weight of disodium 1-hydroxyethane-1,1-diphosphonic acid (HDPA), 0.072% by weight of [2,2'-azobis[2-(2-imidazolin-2-yl)propane]dihydrochloride, 0.072% by weight of sodiumperoxodisulfate solution (15% by weight in water) and water. The degree of neutralization was 71%. The feed per bore was 1.4 kg/h.

The resulting superabsorbent polymer particles were analyzed. The conditions and results are summarized in tables 5 to 7.

Example 12 (not Inventive)

The example was performed analogous to example 11. The feed to the spray dryer consisted of 10.45% by weight of acrylic acid, 33.40% by weight of sodium acrylate, 0.018% by weight of 3-tuply ethoxylated glycerol triacrylate, 0.216% by weight of disodium 1-hydroxyethane-1,1-diphosphonic acid (HDPA), 0.072% by weight of [2,2'-azobis[2-(2-imidazolin-2-yl)propane]dihydrochloride, 0.072% by weight of sodiumperoxodisulfate solution (15% by weight in water) and water.

The resulting superabsorbent polymer particles were analyzed. The conditions and results are summarized in tables 5 to 7.

Example 13 (Inventive)

The example was performed analogous to example 11. The feed to the spray dryer consisted of 10.45% by weight of acrylic acid, 33.40% by weight of sodium acrylate, 0.018% by weight of 3-tuply ethoxylated glycerol triacrylate, 0.216% by weight of disodium 1-hydroxyethane-1,1-diphosphonic acid (HDPA), 0.018% by weight of disodium 2-hydroxy-2-sulfonato acetic acid (HSAA), 0.072% by weight of [2,2'-azobis[2-(2-imidazolin-2-yl)propane]dihydrochloride, 0.072% by weight of sodiumperoxodisulfate solution (15% by weight in water) and water.

The resulting superabsorbent polymer particles were analyzed. The conditions and results are summarized in tables 5 to 7.

Example 14 (Inventive)

The example was performed analogous to example 13. The feed to the spray dryer consisted of 10.45% by weight of acrylic acid, 33.40% by weight of sodium acrylate, 0.018% by weight of 3-tuply ethoxylated glycerol triacrylate, 0.216% by weight of disodium 1-hydroxyethane-1,1-diphosphonic acid (HDPA), 0.036% by weight of disodium 2-hydroxy-2-sulfonato acetic acid (HSAA), 0.072% by weight of [2,2'-azobis[2-(2-imidazolin-2-yl)propane]dihydrochloride, 0.072% by weight of sodiumperoxodisulfate solution (15% by weight in water) and water.

The resulting superabsorbent polymer particles were analyzed. The conditions and results are summarized in tables 5 to 7.

Example 15 (Inventive)

The example was performed analogous to example 13. The feed to the spray dryer consisted of 10.45% by weight of acrylic acid, 33.40% by weight of sodium acrylate, 0.018% by weight of 3-tuply ethoxylated glycerol triacrylate, 0.216% by weight of disodium 1-hydroxyethane-1,1-diphosphonic acid (HDPA), 0.072% by weight of disodium 2-hydroxy-2-sulfonato acetic acid (HSAA), 0.072% by weight of [2,2'-azobis[2-(2-imidazolin-2-yl)propane]dihydrochloride, 0.072% by weight of sodiumperoxodisulfate solution (15% by weight in water) and water.

The resulting superabsorbent polymer particles were analyzed. The conditions and results are summarized in tables 5 to 7.

Examples 16 to 20

All base polymers were surface post-crosslinked with 2.0 wt % ethylene carbonate, 5.0 wt % water and 0.1 wt % aluminum sulfate based on the base polymer as described in WO 2015/110321 A1.

In a Schugi Flexomix® (model Flexomix 160, manufactured by Hosokawa Micron B.V., Doetinchem, the Netherlands) with a speed of 2000 rpm, the base polymer was coated with a surface-postcrosslinker solution by using 2 or 3 round spray nozzle systems (model Gravity-Fed Spray Set-ups, External Mix Typ SU4, Fluid Cap 60100 and Air Cap SS-120, manufactured by Spraying Systems Co, Wheaton, Illinois, USA) and then filled via base polymer feed (70) and dried in a thermal dryer (65) (model NPD 5W-18, manufactured by GMF Gouda, Waddinxveen, the Netherlands) with a speed of the shaft (76) of 6 rpm. The thermal dryer (65) has two paddles with a shaft offset of 90° (80) and a fixed discharge zone (71) with two flexible weir plates (73). Each weir has a weir opening with a minimal weir height at 50% (75) and a maximal weir opening at 100% (74) as shown in FIG. 15 of WO 2015/110321 A1.

The inclination angle α (78) between the floor plate and the thermal dryer was approx. 3°. The weir height of the thermal dryer was between 50 to 100%, corresponding to a residence time of approx. 40 to 150 min, by a product density of approx. 700 to 750 kg/m³. The product temperature in the thermal dryer was in a range of 120 to 165° C. After drying, the surface-post-crosslinked polymer was transported over discharge cone (77) in a cooler (model NPD 5W-18, manufactured by GMF Gouda, Waddinxveen, the Netherlands), to cool down the surface post-crosslinked polymer to approx. 60° C. with a speed of 11 rpm and a weir height of 145 mm. After cooling, the material was sieved with a minimum cut size of 150 μm and a maximum cut size of 850 μm.

6.02 wt. % of an aqueous solution of aluminum trilactate and sorbitan monolaurate (Span® 20), as described in table 9, was additionally added into the cooler using two nozzles in the first third of the cooler. The nozzles were placed below the product bed.

The conditions and results are summarized in tables 8 and 9. The resulting superabsorbent polymer particles were analyzed. The analytical data are summarized in tables 10, 11 and 12.

Example 21

Analogous to the Examples 16 to 20, but, instead of 6.02 wt. % of an aqueous solution of aluminum trilactate and sorbitan monolaurate (Span® 20), 3.17 wt. % of an aqueous solution of aluminum trilactate and sorbitan monolaurate (Span® 20), as described in table 9, was additionally added into the cooler using in one nozzle and 3.35 wt. % of an aqueous solution of sodium hypophosphite, as described in table 9, was additionally added into the cooler using a second nozzle. Both nozzles are placed in the first third of the cooler.

After cooling, the material was sieved with only with a maximum cut size of 850 μm. No additional minimum cut sieve was used.

The conditions and results are summarized in tables 8 and 9. The resulting superabsorbent polymer particles were analyzed. The analytical data are summarized in tables 10, 11 and 12.

TABLE 5

| Process conditions of the polymerization | | | | | |
|---|---|---|---|---|---|
| T gas inlet ° C. | T gas outlet ° C. | T gas IFB ° C. | T IFB ° C. | T CC ° C. | T GDU ° C. |
| 179 | 118 | 106 | 78 | 56 | 47 |

T gas inlet: temperature of the gas prior to the gas distributor (3)
T gas outlet: temperature of the gas leaving the reaction zone (5)
T gas IFB temperature of the gas entering the internal fluidized bed (27) via line (25)
T IFB: temperature of the superabsorbent polymer particles in the fluidized bed (27)
T CC: temperature of the gas leaving the condenser column (12)
T GDU: temperature of the gas leaving the gas drying unit (37)

TABLE 6

| | Properties of the superabsorbent polymer particles (base polymer) | | | | | | |
|---|---|---|---|---|---|---|---|
| Example Unit | Bulk Density kg/m³ | Flowrate g/s | CRC g/g | AUL g/g | RAA wt. % | Ext. 16 h wt. % | Moisture wt. % |
| 11*) | 585 | 10.0 | 45.3 | 20.2 | 0.6950 | 4.7 | 8.7 |
| 12*) | 589 | 10.1 | 48.7 | 19.3 | 0.7150 | 3.4 | 8.9 |
| 13 | 556 | 9.4 | 55.1 | 11.1 | 0.6450 | 5.2 | 8.4 |
| 14 | 528 | 8.9 | 54.1 | 9.5 | 0.7400 | 9.2 | 8.6 |
| 15 | 520 | 8.8 | 57.9 | 9.9 | 0.7300 | 10.2 | 8.3 |

*)comparative example

TABLE 7

| | Particle size distribution of the superabsorbent polymer particles (base polymer) | | | | | | | | | |
|---|---|---|---|---|---|---|---|---|---|---|
| Example Unit | 150 μm μm | 150-200 μm | 200-250 μm | 250-300 μm | 300-400 μm | 400-500 μm | 500-600 μm | 600-710 μm | 710-850 μm | >850 μm Roundness |
| 11*) | 0.3 | 2.3 | 10.4 | 15.5 | 35.8 | 25.3 | 7.8 | 2.1 | 0.5 | 0.0 0.80 |
| 12*) | 0.3 | 2.5 | 10.3 | 15.4 | 35.8 | 25.4 | 7.7 | 2.2 | 0.4 | 0.1 0.79 |
| 13 | 0.3 | 2.4 | 10.4 | 13.9 | 31.4 | 29.4 | 9.0 | 2.5 | 0.5 | 0.2 0.82 |
| 14 | 1.2 | 1.9 | 9.1 | 12.7 | 29.8 | 29.8 | 10.0 | 3.4 | 1.5 | 0.4 0.81 |
| 15 | 0.2 | 1.9 | 9.4 | 12.9 | 30.5 | 30.4 | 10.2 | 3.2 | 1.0 | 0.3 0.80 |

*)comparative example

TABLE 8

Process conditions of the thermal dryer for the surface post-crosslinking (SXL)

| Example Unit | Product Temp. Set Value °C. | Steam Pressure Wave bar | Steam Pressure Jacket bar | Heater T1 °C. | T2 °C. | T3 °C. | T4 °C. | T5 °C. | T6 °C. | Through-put kg/h | Heater Weir % | No. of Nozzles | Pos. of Nozzles |
|---|---|---|---|---|---|---|---|---|---|---|---|---|---|
| 16-21 | 150 | 4.5 | 4.5 | 78 | 97 | 118 | 126 | 139 | 140 | 470 | 75 | 3 | 90/180/270° |

TABLE 9

Process conditions of the surface post-crosslinking (SXL)

| Example | Base polymer | EC (SXL) wt. % bop | Water (SXL) wt. % bop | Al-Sulfate (dry) (SXL) wt. % bop | SHP (Cooler) wt. % bop | Water (Cooler) wt. % bop | Al-Lactate (dry) (Cooler) wt. % bop | Span ® 20 (Cooler) wt. % bop |
|---|---|---|---|---|---|---|---|---|
| 16*) | 11 | 2.0 | 5.0 | 0.10 |  | 5.7 | 0.32 | 0.0025 |
| 17*) | 12 | 2.0 | 5.0 | 0.10 |  | 5.7 | 0.32 | 0.0025 |
| 18 | 14 | 2.0 | 5.0 | 0.10 |  | 5.7 | 0.32 | 0.0025 |
| 19 | 15 | 2.0 | 5.0 | 0.15 |  | 5.7 | 0.32 | 0.0025 |
| 20 | 16 | 2.0 | 5.0 | 0.15 |  | 5.7 | 0.32 | 0.0025 |
| 21*) | 11 | 2.0 | 5.0 | 0.10 | 0.5 | 5.7 | 0.32 | 0.0025 |

EC: Ethylene carbonate
Al-Sulfate aluminum sulfate
SHP sodium hypophosphite
Al-Lactate aluminum trilactate
Span ® 20 sorbitan monolaurate
bop: based on polymer
*)comparative example

TABLE 10

Properties of the superabsorbent polymer particles (after surface post-crosslinking)

| Exp. Unit | CRC g/g | AUL g/g | AUHL g/g | FSC (1 min) g/g · s | SAP Rewet (3 min) g | Vortex s | Caking % | MC wt. % | RAA wt. % | Extr. 16 h wt. % | Bulk Density g/ml | Flowrate g/s |
|---|---|---|---|---|---|---|---|---|---|---|---|---|
| 16*) | 41.5 | 30.0 | 14.4 | 28 | 0.8 | 32 | 17 | 5.9 | 0.037 | 5.2 | 0.627 | 10.5 |
| 17*) | 42.5 | 28.9 | 12.1 | 27 | 0.6 | 33 | 20 | 5.4 | 0.028 | 6.0 | 0.633 | 11.0 |
| 18 | 45.8 | 27.1 | 11.2 | 30 | 0.6 | 31 | 30 | 5.9 | 0.035 | 6.4 | 0.615 | 10.4 |
| 19 | 48.2 | 24.2 | 9.4 | 32 | 0.4 | 26 | 19 | 5.7 | 0.038 | 6.8 | 0.593 | 9.9 |
| 20 | 48.4 | 23.0 | 8.9 | 32 | 0.5 | 29 | 11 | 5.9 | 0.044 | 7.0 | 0.588 | 9.7 |
| 21*) | 41.2 | 29.5 | 13.5 | 27 | 0.6 | 34 | 42 | 5.8 | 0.038 | 5.4 | 0.635 | 11.9 |

*) comparative example

TABLE 11

Color stability of the superabsorbent polymer particles (after surface post-crosslinking), storaged at 70° C. and 80% relative humidity in a climatic test cabinet for 0, 7 and 14 days

| Exp. | HDPA wt. % boaa | HSAA wt. % boaa | SHP wt. % bop | 0 days L | a | b | YI | HC60 | 7 days L | a | b | YI | HC60 | 14 days L | a | b | YI | HC60 |
|---|---|---|---|---|---|---|---|---|---|---|---|---|---|---|---|---|---|---|
| 16*) | 0.3 |  |  | 92.6 | -1.2 | 8.5 | 15.4 | 67.2 | 79.3 | 2.5 | 13.0 | 31.6 | 40.2 | 72.3 | 4.5 | 15.7 | 43.3 | 25.3 |
| 17*) | 0.6 |  |  | 93.2 | -1.2 | 8.9 | 16.1 | 66.5 | 82.1 | 1.1 | 13.1 | 29.6 | 42.7 | 79.5 | 1.8 | 16.0 | 37.7 | 31.4 |
| 18 | 0.6 | 0.05 |  | 93.5 | -1.1 | 9.5 | 17.3 | 65.0 | 83.1 | 1.0 | 13.2 | 29.3 | 43.4 | 80.3 | 1.4 | 15.8 | 36.3 | 33.0 |
| 19 | 0.6 | 0.10 |  | 94.1 | -1.3 | 9.1 | 16.2 | 66.9 | 86.0 | -0.1 | 12.4 | 25.6 | 48.9 | 83.4 | 0.4 | 14.3 | 30.9 | 40.6 |

TABLE 11-continued

Color stability of the superabsorbent polymer particles (after surface post-crosslinking), storaged at 70° C. and 80% relative humidity in a climatic test cabinet for 0, 7 and 14 days

| Exp. | HDPA wt. % boaa | HSAA wt. % boaa | SHP wt. % bop | 0 days | | | | | 7 days | | | | | 14 days | | | | |
|---|---|---|---|---|---|---|---|---|---|---|---|---|---|---|---|---|---|---|
| | | | | L | a | b | Yl | HC60 | L | a | b | Yl | HC60 | L | a | b | Yl | HC60 |
| 20 | 0.6 | 0.20 | | 94.6 | −1.4 | 8.3 | 14.6 | 69.7 | 88.6 | −1.3 | 11.7 | 22.5 | 53.6 | 86.9 | −1.2 | 13.3 | 26.3 | 47.0 |
| 21*) | 0.6 | | 0.5 | 91.3 | −1.4 | 8.8 | 16.2 | 64.8 | 82.6 | 1.0 | 11.0 | 25.0 | 48.7 | 80.0 | 3.0 | 13.0 | 33.3 | 39.1 |

HDPA: disodium 1-hydroxyethane-1,1-diphosphonic acid
HSAA: disodium 2-hydroxy-2-sulfonato acetic acid
SHP sodium hypophosphite
boaa: based on acrylic acid
bop: based on polymer
*) comparative example

TABLE 12

Particle size distribution of the superabsorbent polymer particles (after surface post-crosslinking)

| Example Unit | 45 μm | 45-150 μm | 150-200 μm | 200-250 μm | 250-300 μm | 300-400 μm | 400-500 μm | 500-600 μm | 600-710 μm | 710-850 μm | >850 μm | D50 μm | Roundness |
|---|---|---|---|---|---|---|---|---|---|---|---|---|---|
| 16*) | 0.0 | 0.8 | 3.4 | 11.7 | 15.3 | 38.2 | 24.2 | 4.8 | 1.4 | 0.1 | 0.0 | 308 | 0.80 |
| 17*) | 0.0 | 0.9 | 3.6 | 12.1 | 15.8 | 38.5 | 22.6 | 4.7 | 1.6 | 0.2 | 0.0 | 304 | 0.81 |
| 18 | 0.0 | 0.8 | 3.2 | 11.2 | 14.6 | 37.7 | 25.8 | 5.1 | 1.3 | 0.1 | 0.0 | 313 | 0.80 |
| 19 | 0.0 | 1.1 | 3.6 | 12.1 | 15.5 | 35.8 | 25.7 | 4.9 | 1.3 | 0.1 | 0.0 | 305 | 0.81 |
| 20 | 0.0 | 0.9 | 3.2 | 11.1 | 15.0 | 34.5 | 27.7 | 5.7 | 1.7 | 0.3 | 0.0 | 313 | 0.81 |
| 21*) | 0.1 | 1.5 | 3.3 | 10.0 | 13.4 | 32.6 | 29.0 | 7.4 | 2.4 | 0.2 | 0.1 | 322 | 0.80 |

*) comparative example

The invention claimed is:

1. A process for producing long-term color stable superabsorbent polymer particles, comprising polymerizing a monomer solution comprising
   a) partly neutralized acrylic acid,
   b) at least one crosslinker,
   c) at least one initiator,
   d) 0.1 to 0.6% by weight of 1-hydroxyethane-1,1-diphosphonic acid or a salt thereof based on the acrylic acid prior to neutralization, and
   e) 0.05 to 0.5% by weight of 2-hydroxy-2-sulfonatoacetic acid or a salt thereof based on the acrylic acid prior to neutralization,
   drying the resulting polymer gel, optionally grinding and classifying the resulting dried polymer gel, and optionally thermally post-crosslinking and cooling the resulting polymer particles.

2. The process according to claim 1, wherein a degree of neutralization of the partly neutralized acrylic acid is from 50 to 85 mol %.

3. The process according to claim 1, wherein the superabsorbent polymer particles are thermally post-crosslinked.

4. The process according to claim 1 wherein the resulting polymer particles have a Hunter 60 value (HC60) after 28 days of aging at 60° C. and a relative humidity of 86% of at least 47.

5. The process according to claim 1 wherein the resulting polymer particles have a Hunter 60 value (HC60) after 28 days of aging at 60° C. and a relative humidity of 86% of at least 55.

* * * * *